(12) United States Patent
Shapiro

(10) Patent No.: US 9,198,763 B2
(45) Date of Patent: *Dec. 1, 2015

(54) SURGICAL TECHNIQUE USING A CONTOURED ALLOGRAFT CARTILAGE AS A SPACER OF THE CARPO-METACARPAL JOINT OF THE THUMB OR TARSO-METATARSAL JOINT OF THE TOE

(71) Applicant: Paul S. Shapiro, Bloomfield Hills, MI (US)

(72) Inventor: Paul S. Shapiro, Bloomfield Hills, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/469,785

(22) Filed: Aug. 27, 2014

(65) Prior Publication Data

US 2015/0005891 A1 Jan. 1, 2015

Related U.S. Application Data

(63) Continuation of application No. 13/020,939, filed on Feb. 4, 2011, now Pat. No. 8,834,568.

(60) Provisional application No. 61/301,310, filed on Feb. 4, 2010.

(51) Int. Cl.
*A61F 2/08* (2006.01)
*A61F 2/42* (2006.01)

(52) U.S. Cl.
CPC ............... *A61F 2/4261* (2013.01); *A61F 2/08* (2013.01)

(58) Field of Classification Search
CPC ........... A61F 2/08; A61F 2/42; A61F 2/4261; A61F 2/0805; A61F 2/0811; A61F 2/30724; A61F 2/30734; A61F 2/30756; A61F 2/3603; A61F 2/3872

USPC ............... 623/21.11–21.15, 16.11, 14.12, 623/17.11–17.16; 606/247–249
See application file for complete search history.

(56) References Cited

U.S. PATENT DOCUMENTS

| | | |
|---|---|---|
| 3,415,613 A | 12/1968 | Wallden |
| 4,502,161 A | 3/1985 | Wall |
| 4,599,086 A | 7/1986 | Doty |
| 4,892,545 A | 1/1990 | Day et al. |
| 4,944,919 A | 7/1990 | Powell |

(Continued)

OTHER PUBLICATIONS

Nilsson, A. et al., "Results from a degradable TMC Joint space (Artelon) compared with tendon arthroplasty", Journal of Hand Surgery (AM), 2005, vol. 30:2, pp. 380-389.

(Continued)

*Primary Examiner* — Alvin Stewart
(74) *Attorney, Agent, or Firm* — The Dobrusin Law Firm, PC

(57) ABSTRACT

A spacer for implantation into a subject is provided that includes a sterilized piece of cartilaginous allograft tissue. The piece forms a Y-shape with a base adapted to insert within a first carpo-metacarpal joint or carpo-metatarsal joint of the subject, and has a first area adapted to secure to a trapezium bone adjoining the joint, and a second arm adapted to secure to a proximal metacarpal or metatarsal bone adjoining the joint. A procedure for implanting the spacer includes exposing a target joint and abrading a bone surface interior to the joint to induce surface bleeding. The spacer base is then inserted into the joint. The spacer first arm is adhered to the first bone of the joint and the spacer second arm is adhered to the second bone of the joint. A kit is also provided for surgical implantation of the spacer.

20 Claims, 1 Drawing Sheet

(56) References Cited

U.S. PATENT DOCUMENTS

| | | | |
|---|---|---|---|
| 4,969,909 A | 11/1990 | Barouk | |
| 5,067,964 A | 11/1991 | Richmond et al. | |
| 5,171,322 A | 12/1992 | Kenny | |
| 5,683,466 A | 11/1997 | Vitale | |
| 5,899,939 A | 5/1999 | Boyce et al. | |
| 6,007,580 A | 12/1999 | Lehto et al. | |
| 6,017,366 A | 1/2000 | Berman | |
| 6,093,205 A | 7/2000 | McLeod et al. | |
| 6,206,883 B1 | 3/2001 | Tunc | |
| 6,206,923 B1 | 3/2001 | Boyd et al. | |
| 6,371,985 B1 | 4/2002 | Goldberg | |
| 6,468,314 B2 | 10/2002 | Schwartz et al. | |
| 6,562,073 B2 | 5/2003 | Foley | |
| 6,626,944 B1 | 9/2003 | Taylor | |
| 6,629,997 B2 | 10/2003 | Mansmann | |
| 6,699,252 B2 | 3/2004 | Farr et al. | |
| 7,037,342 B2 | 5/2006 | Nilsson et al. | |
| 7,044,968 B1 | 5/2006 | Yaccarino et al. | |
| 7,163,563 B2 | 1/2007 | Schwartz et al. | |
| 7,244,273 B2 | 7/2007 | Pedersen et al. | |
| 7,255,712 B1 | 8/2007 | Steinberg | |
| 7,297,161 B2 | 11/2007 | Fell | |
| 7,427,293 B2 | 9/2008 | Nycz et al. | |
| 7,476,250 B1 | 1/2009 | Mansmann | |
| 7,507,253 B2 | 3/2009 | Nordquist | |
| 7,585,316 B2 | 9/2009 | Trieu | |
| 7,611,653 B1 | 11/2009 | Elsner et al. | |
| 7,744,630 B2 | 6/2010 | Lancial | |
| 7,763,051 B2 | 7/2010 | Labrom et al. | |
| 7,871,440 B2 | 1/2011 | Schwartz et al. | |
| 7,901,432 B2 | 3/2011 | Zucherman et al. | |
| 7,963,983 B2 | 6/2011 | Cerundolo | |
| 8,077,950 B2 | 12/2011 | Tsougarakis et al. | |
| 8,100,983 B2 | 1/2012 | Schulte | |
| 8,152,847 B2 | 4/2012 | Strzepa et al. | |
| 8,187,326 B2 | 5/2012 | Hammer et al. | |
| 8,834,568 B2 * | 9/2014 | Shapiro | 623/14.12 |
| 2003/0039676 A1 | 2/2003 | Boyce et al. | |
| 2003/0055502 A1 | 3/2003 | Lang et al. | |
| 2003/0055511 A1 | 3/2003 | Schryver et al. | |
| 2003/0093152 A1 | 5/2003 | Pedersen et al. | |
| 2003/0212456 A1 | 11/2003 | Lipchitz et al. | |
| 2004/0030388 A1 | 2/2004 | Null et al. | |
| 2004/0093081 A1 | 5/2004 | Nilsson et al. | |
| 2004/0143344 A1 | 7/2004 | Malaviya et al. | |
| 2004/0158245 A1 | 8/2004 | Chin | |
| 2004/0210218 A1 | 10/2004 | Dixon et al. | |
| 2005/0033434 A1 | 2/2005 | Berry | |
| 2005/0075641 A1 | 4/2005 | Singhatat et al. | |
| 2005/0101957 A1 | 5/2005 | Buskirk et al. | |
| 2005/0214340 A1 | 9/2005 | Erbe et al. | |
| 2006/0149261 A1 | 7/2006 | Nilsson et al. | |
| 2006/0241777 A1 | 10/2006 | Partin et al. | |
| 2007/0038303 A1 | 2/2007 | Myerson et al. | |
| 2007/0093896 A1 | 4/2007 | Malinin | |
| 2007/0118218 A1 | 5/2007 | Hooper | |
| 2007/0135918 A1 | 6/2007 | Malinin | |
| 2007/0149982 A1 | 6/2007 | Lyons | |
| 2007/0179607 A1 | 8/2007 | Hodorek et al. | |
| 2007/0276489 A1 | 11/2007 | Bindseil et al. | |
| 2007/0293947 A1 | 12/2007 | Mansmann | |
| 2008/0177386 A1 | 7/2008 | Cerundolo | |
| 2008/0255665 A1 | 10/2008 | Weissberg | |
| 2008/0269762 A1 | 10/2008 | Simon et al. | |
| 2008/0269908 A1 | 10/2008 | Warburton | |
| 2008/0275555 A1 | 11/2008 | Makower et al. | |
| 2009/0012617 A1 | 1/2009 | White et al. | |
| 2009/0048672 A1 | 2/2009 | Essenmacher | |
| 2009/0088846 A1 | 4/2009 | Myung et al. | |
| 2009/0226068 A1 | 9/2009 | Fitz et al. | |
| 2009/0234396 A1 | 9/2009 | Medoff | |
| 2009/0287307 A1 | 11/2009 | Parry et al. | |
| 2009/0318976 A1 | 12/2009 | Gabriel et al. | |
| 2010/0042151 A1 | 2/2010 | Anderson | |
| 2010/0049322 A1 | 2/2010 | McKay | |
| 2010/0057215 A1 | 3/2010 | Graham | |
| 2010/0082112 A1 | 4/2010 | Keller et al. | |
| 2010/0106254 A1 | 4/2010 | DelSignore | |
| 2010/0131008 A1 | 5/2010 | Overes et al. | |
| 2010/0145387 A1 | 6/2010 | Bruneau et al. | |
| 2010/0145452 A1 | 6/2010 | Blaylock et al. | |
| 2010/0168864 A1 | 7/2010 | White et al. | |
| 2011/0022091 A1 | 1/2011 | Anderson et al. | |
| 2011/0040334 A1 | 2/2011 | Kaes et al. | |
| 2011/0060366 A1 | 3/2011 | Heim et al. | |
| 2011/0172709 A1 | 7/2011 | Lyons et al. | |
| 2011/0190887 A1 * | 8/2011 | Shapiro | 623/14.12 |
| 2011/0238180 A1 | 9/2011 | Fritz et al. | |
| 2012/0143339 A1 | 6/2012 | Voellmicke et al. | |
| 2015/0005891 A1 * | 1/2015 | Shapiro | 623/21.12 |

OTHER PUBLICATIONS

Choung, E. et al., "Foreign-Body Reaction to the Artelon CMC Joint Spacer; Case report", Journal of Hand Surgery (Am), 2008, vol. 33:9, pp. 1617-1620.

* cited by examiner

SURGICAL TECHNIQUE USING A CONTOURED ALLOGRAFT CARTILAGE AS A SPACER OF THE CARPO-METACARPAL JOINT OF THE THUMB OR TARSO-METATARSAL JOINT OF THE TOE

CLAIM OF BENEFIT OF FILING DATE

The present application is a continuation application of U.S. application Ser. No. 13/020,939, filed Feb. 4, 2011, which claims the benefit of U.S. Provisional Application Ser. No. 61/301,310, filed Feb. 4, 2010, all of which are incorporated herein by reference for all purposes.

FIELD OF THE INVENTION

The present invention in general relates to a spacer used to treat basal joint arthritis of the thumb or toe and in particular to the surgical implantation of an allograft of knee cartilage as the spacer.

BACKGROUND OF THE INVENTION

A variety of surgical procedures have been developed for the treatment of basal joint osteoarthritis (OA—arthritis causing wearing down and changes in joint surfaces) of the thumb. These include ligament (band of tissue that connects bones) reconstruction (repair through rebuilding), metacarpal osteotomy (bone removed or divided), trapezium excision (surgical procedure of hand joint), soft tissue interposition (repositioning) with or without ligament reconstruction, trapeziometacarpal (bones located in hand) arthrodesis (surgical joint immobilization), silicone (polymeric organic compound) arthroplasty (restoration of a joint), hematoma (mass of clotted blood) and distraction (separation) arthroplasty, and total joint arthroplasty. Problems with persistent pain and poor function have been reported for each of these procedures.

Recently, the ARTELON® CMC (carpo-metacarpal) spacer composed of a biodegradable (broken down by body) polycaprolactone-based polyurethane urea has been introduced for the treatment of basal joint osteoarthritis. A three year prospective pilot study demonstrated that all patients treated with the ARTELON® CMC spacer were stable clinically, had no signs of synovitis (inflammation of synovial membrane), and were pain free. (Nilsson, A., Liljensten, E., Bergstrom, C., Sollerman, C. "Results from a degradable TMC Joint Spacer (Artelon) compared with tendon arthroplasty". *Journal of Hand Surgery (Am)*, 30:2, 2005 380-389.) However, clinical complications have been reported with the use of this implant, causing many surgeons to abandon its use. A recent case report demonstrated a foreign-body tissue reaction associated the ARTELON® CMC spacer, requiring implant removal and revision with hematoma and distraction arthroplasty. (Choung, E. W., Tan, V. "Foreign-Body Reaction to the Artelon CMC joint Spacer: Case report". *Journal of Hand Surgery (Am.)*. 33:9, 2008 1617-1620.)

Thus, there is a need for less reactive and smoother surfaced allograft of knee meniscal tissue as an implant will provide improved pain relief and hand function, while reducing complications in patients being treated surgically for osteoarthritis of the thumb.

SUMMARY OF THE INVENTION

A spacer for implantation into a subject is provided that includes a sterilized piece of cartilaginous allograft tissue. The piece forms a Y-shape with a base adapted to insert within a first carpo-metacarpal joint or carpo-metatarsal joint of the subject, and has a first arm adapted to secure to a trapezium bone adjoining the joint, and a second arm adapted to secure to a proximal metacarpal or metatarsal bone adjoining the joint.

A procedure for implanting the spacer includes exposing a target joint and abrading a bone surface interior to the joint to induce surface bleeding. The spacer base is then inserted into the joint in contact with the bleeding surface and the intact surface the other bone defining the joint. The spacer first arm is adhered to the first bone of the joint and the spacer second arm is adhered to the second bone of the joint. A kit is also provided for surgical implantation of the spacer.

DETAILED DESCRIPTION OF THE INVENTION

The present invention has utility in the treatment of basal joint arthritis of the thumb with reduced complications. A replacement tissue spacerspacer is formed in a "Y" shape and shown generally at 10 with a base 12 and a first arm 14 and a second arm 16 and sterilized according to conventional tissue preparation techniques, such as those detailed in U.S. Pat. Nos. 3,415,613 and 4,944,919, and by other conventional techniques illustratively including chemical sterilization such as with ethylene oxide; radiation sterilization such as with gamma radiation; and thermal sterilization. It is appreciated that surfactant decellularization is also operative herein to retain a proteinaceous scaffold free of donor cells and therefore precludes antigenicity.

Tissues from which an inventive spacer 10 is formed are harvested from a cadaver. It is appreciated that the cadaver need not be of the same species as the recipient. Cartilaginous tissues suitable for excision to form an spacer 10 illustratively include those of the knee meniscus, mandibular condyle of the temporormandibular joint, and intervertebral disks. Preferably, the tissue is fibrocartilage having an appreciable amount of collagen type I. Hyaline- and elastic-rich cartilage are also operative as a source of tissue for spacer 10. By way of example, knee meniscus tissue is obtained from a cadaver. Preferably, cadaver tissue is from the same species as the subject to limit the possibility of an immune response to the spacer 10.

Figure 1:
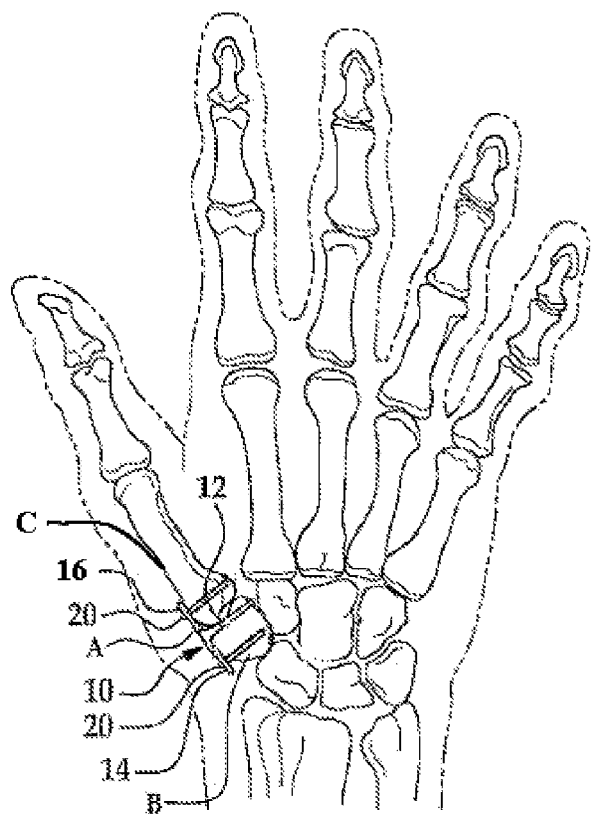
FIG. 1 is a schematic depicting an inventive spacer secured within the first carpo-metacarpal joint.
Figure 2:
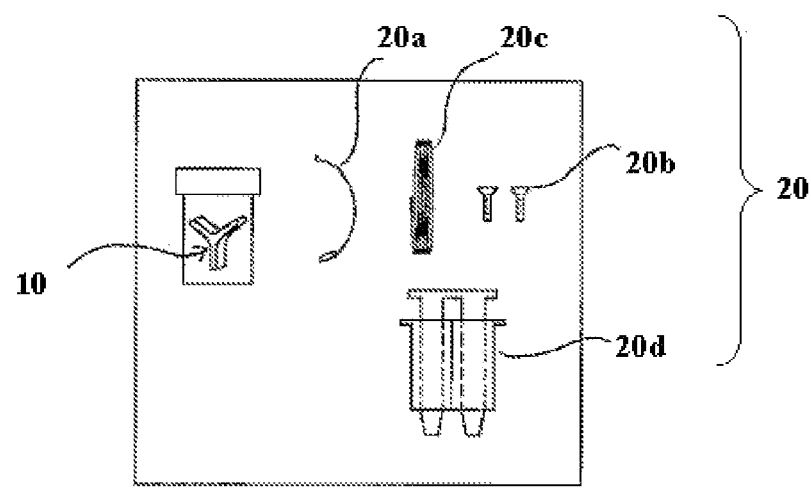
FIG. 2 is a top view of a kit containing the inventive spacer.

The spacer 10 is placed with the base 12 of the "Y" spacer 10 within the first carpo-metacarpal (CMC-1) joint with the arms 14 and 16 of the "Y" secured to the trapezium bone B rid metacarpal bone C defining CMC-1, respectively. It is appreciated that an inventive spacer and procedure also suitable with only dimensional modifications of the spacer for repair of the corresponding metatarsal joint anatomy. Securements 20 for the arms are illustratively performed with tissue adhesives, suture anchors, screws, sutures, or a combination thereof as detailed in FIG. 1. Preferably, the first arm 14 of the Y and the second arm 16 are within 30% of being equal in length.

A kit is provided that includes a spacer 10 along with instructions for the surgical implantation of the spacer into the first carpo-metacarpal joint. Preferably, the spacer is provided in a sterile, implement-compatible solution Optionally, the kit includes securements 20 for adhering the arms 14 and 16 of the spacer 10 to the trapezium bone 13 aid metacarpal bones C, respectively. Optionally, the kit also includes a trimming instrument such as a scissors for the spacer 10 to the anatomy of the subject CMC-1 joint. The securements 20 are a suture anchor 20a, a screen 20b, suture ligament 20c, or tissue adhesive 20d.

The procedure for implantation corresponds to that detailed for the prior art ARTELON® CMC-1 spacer with the proviso that the inventive spacer is formed of sterile cadaver cartilagenous tissue and not biodegradable polyurethaneurea. An inventive spacer is immersed in sterile saline or other physiologically suitable liquid to assure adequate hydration. Typical soaking times for an inventive spacer re from 3 to 30 minutes and preferably at least 5 minutes. The joint of insertion, whether CMC-1 or a metatarsal joint analog, is opened with a dorsal incision. A periosteal flap is dissected from the trapezium bone including the joint capsule. The resultant flap is extended for a length of approximately 1 to 2 centimeters. It is appreciated that the flap is readily dissected in distal or proximal directions. The distal joint surface is then resected along with approximately 1 to 2 millimeters of subcondral bone of the articular surface of the trapezium bone. The articular surface of the metacarpal bone of CMC-1 or the equivalent metatarsal bone is preferably left intact. The goal of this resection is to create a bleeding surface on the trapezium bone to promote cellular regrowth and adhesion to the inventive spacer while the intact surface of the metacarpal or metatarsal bone, depending on the situs of insertion, is left intact to create a new joint surface against which articulation can occur. Preferably, osteophytes are then removed from along the joint lines and relative positions are marked for the arms 14 and 16. The cortical bone in the marked area is then burred to create a bleeding surface against which the arms 14 and 16 will subsequently be in contact. The burring is intended to only be sufficiently deep so as to achieve bleeding surfaces. Fixation of the arms 14 and 16 readily occurs with suture anchors, screws, or sutures by methods conventional to the art. Subsequent to fixation of the arms 14 and 16 to the trapezium bone B and metacarpal or metatarsal bone C, depending on the joint situs, by conventional means, the periosteal flap is then reattached and the skin closed. With some weeks of casting, a stabilized and flexible joint results.

The invention claimed is:

1. An implant for implantation into a subject comprising: a sterilized piece of cartilaginous allograft tissue harvested from a cadaver from a knee meniscus, a mandibular condyle of the temporomandibular joint, or intervertebral disks, the piece forming a Y shape with a base sized to insert within a first carpo-metacarpal joint of the subject;
    a first arm adapted to secure to a trapezium bone adjoining the joint; and
    a second arm adapted to secure to a proximal metacarpal bone adjoining the joint.

2. The implant of claim 1 wherein the second arm has a length that is within 30% of a length of the first arm.

3. The implant of claim 1 further comprising a first securement for securing the first arm to the trapezium bone and a second securement for securing the second arm to the metacarpal bone.

4. The implant of claim 3 where the first securement is one of tissue adhesives, suture anchors, screws, sutures, or a combination thereof.

5. The implant of claim 1 wherein the tissue is knee meniscus tissue.

6. The implant of claim 1 wherein the tissue is from a cadaver of the same species as the subject.

7. A procedure for implanting the implant of claim 1 comprising:
    exposing a target joint;
    inducing bleeding on a surface of a first bone of said joint;
    inserting the base of the implant into contact with the surface and an intact second bone of the joint; and
    screwing or suturing the first arm to the first bone and the second to the second bone.

8. The procedure of claim 7 wherein the joint being repaired is a carpo-metacarpal joint.

9. A kit comprising:
    an implant according to claim 1, along with instructions for the surgical implantation thereof into first carpo-metacarpal joint with the arms of the "Y" secured to trapezium and metacarpal bones defining joint.

10. The kit of claim 9 and further comprising: at least two securements each independently being a suture anchor, a screw, or a suture.

11. The kit of claim 10 wherein the at least two securements include suture anchors.

12. The kit of claim 10 wherein the at least two securements include screws.

13. The kit of claim 9 and further comprising: a tissue adhesive and applicator therefor.

14. An implant for implantation into a subject comprising:
    a sterilized piece of cartilaginous allograft tissue harvested from a cadaver from a knee meniscus, a mandibular condyle of the temporomandibular joint, or intervertebral disks, the piece forming a Y shape with a base sized to insert within a first carpo-metacarpal joint or tarso-metatarsal joint of the subject, the cartilaginous allograft tissue comprising fibrocartilage having collagen type I;
    a first arm adapted to secure to a first bone adjoining the joint; and
    a second arm adapted to secure to a second bone, the second bone beings proximal metacarpal or metatarsal bone adjoining the joint.

15. The implant of claim 14, wherein the first arm of the Y shape and the second arm are within 30% of being equal in length.

16. The implant of claim 14, wherein said implant has a base sized to insert within the first carpo-metacarpal point and comprises a first securement for securing the first arm to the first bone, the first bone being a trapezium bone, and a second securement for securing the second arm to the metacarpal bone.

17. The implant of claim 16, wherein the first securement is one of tissue adhesives, suture anchors, screws, sutures, or a combination thereof.

18. The implant of claim 14, wherein said tissue of cadaver of the same species as the subject.

19. An implant for implantation into a subject comprising: a sterilized piece of cartilaginous allograft tissue excised from a knee meniscus, a mandibular condyle of the temporomandibular joint, or intervertebral disks, the piece forming a Y shape with a base sized to insert within a first carpo-metacarpal joint of the subject;
    a first arm adapted to secure to a trapezium bone adjoining the joint; and
    a second arm adapted to secure to a proximal metacarpal bone adjoining the joint, the second arm having a length that is within 30% of a length of the first arm, wherein the first arm and the second arm are adapted to secure to the trapezium and metacarpal bones using a suture or a screw.

20. The implant of claim 19 wherein the tissue is harvested from a cadaver of the same species as the subject.

\* \* \* \* \*